United States Patent
Baraldi et al.

(10) Patent No.: US 7,767,685 B2
(45) Date of Patent: Aug. 3, 2010

(54) ADENOSINE A2B RECEPTOR ANTAGONISTS

(75) Inventors: Pier Giovanni Baraldi, Ferrara (IT); Pier Andrea Borea, Ferrara (IT); Allan Moorman, Durham, NC (US); Mojgan Aghazadeh Tabrizi, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 587 days.

(21) Appl. No.: 11/767,575

(22) Filed: Jun. 25, 2007

(65) Prior Publication Data

US 2008/0045549 A1  Feb. 21, 2008

Related U.S. Application Data

(60) Provisional application No. 60/817,309, filed on Jun. 29, 2006.

(51) Int. Cl.
| | |
|---|---|
| *C07D 473/06* | (2006.01) |
| *A61K 31/522* | (2006.01) |
| C07D 231/14 | (2006.01) |
| A61P 11/06 | (2006.01) |
| A61P 3/10 | (2006.01) |
| A61P 19/02 | (2006.01) |
| A61P 37/08 | (2006.01) |

(52) U.S. Cl. ............... 514/263.2; 544/270; 548/374.1
(58) Field of Classification Search ............... 544/270; 514/263.2

See application file for complete search history.

(56) References Cited

U.S. PATENT DOCUMENTS

| | | | | |
|---|---|---|---|---|
| 6,825,349 | B2 | 11/2004 | Kalla et al. | 544/267 |
| 6,977,300 | B2 | 12/2005 | Kalla et al. | 544/269 |
| 7,205,403 | B2 | 4/2007 | Baraldi et al. | 544/118 |
| 7,618,962 | B2* | 11/2009 | Wang et al. | 514/234.2 |
| 2003/0207879 | A1 | 11/2003 | Baraldi et al. | 514/228.5 |
| 2005/0101778 | A1 | 5/2005 | Kalla et al. | 544/269 |
| 2005/0233328 | A1 | 10/2005 | Berghs et al. | 435/6 |
| 2006/0058322 | A1* | 3/2006 | Zeng et al. | 514/263.2 |
| 2006/0159627 | A1* | 7/2006 | Zeng et al. | 424/45 |
| 2006/0293283 | A1* | 12/2006 | Kalla et al. | 514/81 |
| 2007/0219221 | A1* | 9/2007 | Zeng et al. | 514/263.2 |
| 2008/0085908 | A1* | 4/2008 | Kalla et al. | 514/263.2 |
| 2008/0153856 | A1* | 6/2008 | Kalla et al. | 514/263.2 |
| 2008/0176872 | A1* | 7/2008 | Lamb et al. | 514/263.2 |
| 2008/0280926 | A1* | 11/2008 | Palle et al. | 514/263.2 |
| 2008/0293705 | A1* | 11/2008 | Wilson et al. | 514/227.8 |
| 2009/0069289 | A1* | 3/2009 | Neagu et al. | 514/210.21 |
| 2009/0099212 | A1* | 4/2009 | Zablocki et al. | 514/263.2 |
| 2009/0137624 | A1* | 5/2009 | Lamb et al. | 514/303 |
| 2009/0143377 | A1* | 6/2009 | Ng et al. | 514/234.2 |
| 2009/0298744 | A1* | 12/2009 | Palle et al. | 514/3 |

* cited by examiner

*Primary Examiner*—Mark L Berch
(74) *Attorney, Agent, or Firm*—Paivi Kukkola

(57) ABSTRACT

The present invention provides compounds of the formula

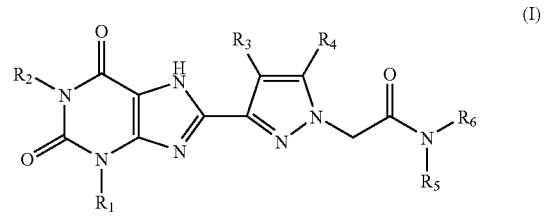

(I)

which are adenosine $A_{2B}$ receptor antagonists and, thus, may be employed for the treatment of conditions and diseases mediated by the adenosine $A_{2B}$ receptor activity. Such conditions include, but are not limited to, chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

7 Claims, No Drawings

ADENOSINE A2B RECEPTOR ANTAGONISTS

This application claims the benefit of U.S. Provisional Application No. 60/817,309, filed Jun. 29, 2006 incorporated herein by reference in its entirety.

The present invention relates to 8-pyrazol-xanthine derivatives, pharmaceutical compositions containing them, and methods of treating conditions and diseases mediated by the adenosine $A_{2B}$ receptor activity, by employing such compounds.

Accordingly, the present invention provides compounds of the formula

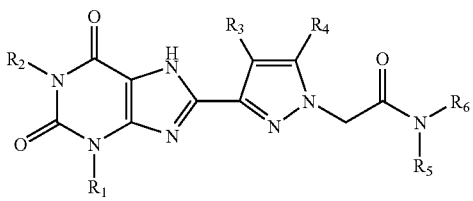

wherein
- $R_1$ and $R_2$ are, independently from each other, $C_1$-$C_6$ alkyl optionally substituted by $C_1$-$C_4$ alkoxy, $C_3$-$C_6$ cycloalkyl, $C_2$-$C_4$ alkenyl, $C_2$-$C_4$ alkynyl or monocyclic aryl that may be optionally substituted by 1-3 substituents selected from the group consisting of $C_1$-$C_4$ alkyl, trifluoromethyl, halo, hydroxy, $C_1$-$C_4$ alkoxy, methylenedioxy, thiol, $C_1$-$C_4$ alkylthio, cyano, carboxy, $C_1$-$C_4$ alkoxycarbonyl, $C_1$-$C_4$ alkylthiono or $C_1$-$C_4$ alkylsulfonyl;
- $R_3$ is hydrogen or halogen;
- $R_4$ and $R_5$ are, independently from each other, hydrogen or $C_1$-$C_4$ alkyl;
- $R_6$ is aryl or heteroaryl each of which may be optionally substituted by 1-3 substituents selected from the group consisting of $C_1$-$C_6$alkyl, trifluoromethyl, $C_3$-$C_6$ cycloalkyl, halo, hydroxy, $C_1$-$C_6$ alkoxy, methylenedioxy, ethylenedioxy, $C_1$-$C_6$ alkanoyl, $C_1$-$C_{10}$ alkanoyloxy, $C_6$-$C_{10}$ aryloxy, amino, $C_1$-$C_6$ alkylamino, di($C_1$-$C_6$ alkyl)amino, thiol, $C_1$-$C_6$ alkylthio, $C_6$-$C_{10}$ arylthio, nitro, cyano, carboxy, $C_1$-$C_6$ alkoxycarbonyl, carbamoyl, $C_1$-$C_6$ alkylthiono, $C_1$-$C_6$ alkylsulfonyl or $C_6$-$C_{10}$ arylsulfonyl;

or a pharmaceutically acceptable salt thereof.

The compounds of the present invention are adenosine $A_{2B}$ receptor antagonists and, thus, may be employed for the treatment of conditions and diseases mediated by the adenosine $A_{2B}$ receptor activity. Such conditions include, but are not limited to, chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

The 8-pyrazol-xanthine derivatives of the present invention may also be employed as radioligands for studying biological activity associated with the adenosine receptors, in particular, the adenosine $A_{2B}$ receptor Certain 8-pyrazol-xanthine derivatives have been disclosed previously as adenosine $A_{2B}$ receptor antagonists, e.g., those as described in U.S. Pat. Nos. 7,205,403 and 6,825,349.

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted alkyl groups, i.e., straight- or branched-chain hydrocarbon groups having 1-20 carbon atoms, preferably 1-10 carbon atoms, more preferably 1-7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more, preferably 1-3, of the following groups: halo, hydroxy, alkanoyl, alkoxy, cycloalkyl, cycloalkoxy, alkanoyloxy, thiol, alkylthio, alkylthiono, sulfonyl, sulfamoyl, carbamoyl, cyano, carboxy, acyl, aryl, aryloxy, alkenyl, alkynyl, aralkoxy, guanidino, optionally substituted amino, heterocyclyl including imidazolyl, furyl, thienyl, thiazolyl, pyrrolidyl, pyridyl, pyrimidyl and the like.

The term "lower alkyl" refers to those alkyl groups as described above having 1-6, preferably 2-4 carbon atoms.

The term "alkenyl" refers to any of the above alkyl groups having at least two carbon atoms and further containing a carbon-to-carbon double bond at the point of attachment. Groups having 2-4 carbon atoms are preferred.

The term "alkynyl" refers to any of the above alkyl groups having at least two carbon atoms and further containing a carbon-to-carbon triple bond at the point of attachment. Groups having 2-4 carbon atoms are preferred.

The term "alkylene" refers to a straight-chain bridge of 1-6 carbon atoms connected by single bonds, e.g., —($CH_2$)x—, wherein x is 1-6, in those cases where x is greater than 1, the chain may be interrupted with one or more heteroatoms selected from O, S, S(O), $S(O)_2$, CH=CH, C≡C or NR, wherein R may be hydrogen, alkyl, alkenyl, alkynyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl, cyclohexenyl, 4,4-dimethylcyclohex-1-yl, cyclooctenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo

[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

In the definitions listed herein, when a reference to an alkyl, cycloalkyl, alkenyl or alkynyl group is made as part of the term, a substituted alkyl, cycloalkyl, alkenyl or alkynyl group is also intended.

The term "alkoxy" refers to alkyl-O—.
The term "cycloalkoxy" refers to cycloalkyl-O—.
The term "alkanoyl" refers to alkyl-C(O)—.
The term "cycloalkanoyl" refers to cycloalkyl-C(O)—.
The term "alkenoyl" refers to alkenyl-C(O)—.
The term "alkynoyl" refers to alkynyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.

The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, optionally substituted cycloalkyl, halo, hydroxy, alkoxy, methylenedioxy, ethylenedioxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described above under aryl. Preferably, the monocyclic aryl is substituted by 1-3 substituents selected from the group consisting of halogen, cyano, or trifluoromethyl.

In the definitions listed herein, when a reference to an aryl group is made as part of the term, a substituted aryl group is also intended.

The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl(pyridyl), pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, 1H-purine-2,6(3H,7H)-dione, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" refers to those heterocyclic groups described above substituted with 1, 2 or 3 substituents selected from the group consisting of the following:
  (a) optionally substituted alkyl;
  (b) hydroxyl (or protected hydroxyl);
  (c) halo;
  (d) oxo, i.e., =O;
  (e) optionally substituted amino;
  (f) alkoxy;
  (g) cycloalkyl;
  (h) carboxy;
  (i) heterocyclooxy;
  (j) alkoxycarbonyl, such as unsubstituted lower alkoxycarbonyl;
  (k) thiol;

(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; and
(w) aryl optionally substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heterocycloalkyl" refers to nonaromatic heterocyclic groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., halogen, cyano, nitro, trifluoromethyl, lower alkyl, or lower alkoxy.

The term "heterocycloalkanoyl" refers to heterocycloalkyl-C(O)—.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, alkenoyl, alkynoyl, aroyl, heterocycloalkanoyl, heteroaroyl, aralkanoyl, heteroaralkanoyl and the like.

The term "substituted acyl" refers to those acyl groups described above wherein the alkyl, cycloalkyl, alkenyl, alkynyl, aryl, heterocycloalkyl, heteroaryl, aralkyl, or heteroaralkyl group is substituted as described herein above, respectively.

The term "acylamino" refers to alkanoylamino, aroylamino, heteroaroylamino, aralkanoylamino, heteroaralkanoylamino and the like.

The term "halogen" or "halo" refers to fluorine, chlorine, bromine and iodine.

Pharmaceutically acceptable salts of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

As described herein above, the present invention provides 8-pyrazol-xanthine derivatives of formula (I), pharmaceutical compositions containing them, methods for preparing said compounds, and methods of treating conditions mediated by the adenosine A$_{2B}$ receptor including, but not limited to, chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine A$_{2B}$ receptors, e.g., retinopathy of prematurity, macular degeneration, and diabetic retinopathy; and cardiac diseases including hyperplasia consequent to hypertension, arteriosclerosis, and heart attack; by administration of a therapeutically effective amount of a compound of the present invention, or a pharmaceutical composition thereof.

Preferred are the compounds of formula (I) wherein
R$_3$ is hydrogen;

or a pharmaceutically acceptable salt thereof.

Further preferred are the compounds of formula (I) wherein
R$_5$ is hydrogen;
R$_6$ is monocyclic aryl which may be optionally substituted by 1-3 substituents selected from the group consisting of C$_1$-C$_6$ alkyl, trifluoromethyl, C$_3$-C$_6$ cycloalkyl, halo, hydroxy, C$_1$-C$_6$ alkoxy, methylenedioxy, ethylenedioxy, C$_1$-C$_6$ alkanoyl, C$_1$-C$_6$ alkanoyloxy, C$_6$-C$_{10}$ aryloxy, amino, C$_1$-C$_6$ alkylamino, di(C$_1$-C$_6$ alkyl)amino, thiol, C$_1$-C$_6$alkylthio, C$_6$-C$_{10}$ arylthio, nitro, cyano, carboxy, C$_1$-C$_6$alkoxycarbonyl, carbamoyl, C$_1$-C$_6$ alkylthiono, C$_1$-C$_6$ alkylsulfonyl or C$_6$-C$_{10}$ arylsulfonyl;

or a pharmaceutically acceptable salt thereof.

More preferred are the compounds of formula (I) wherein
R$_1$ and R$_2$ are, independently from each other, C$_1$-C$_3$ alkyl optionally substituted by cyclopropyl, —CH=CH$_2$, —C≡CH or phenyl;

or a pharmaceutically acceptable salt thereof.

Most preferred are the compounds of formula (I) wherein
R$_4$ is methyl;

or a pharmaceutically acceptable salt thereof.

The compounds of the invention depending on the nature of the substituents may possess one or more asymmetric centers. The resulting diastereoisomers, optical isomers, i.e., enantiomers, and geometric isomers, and mixtures thereof, are encompassed by the instant invention.

Particular embodiments of the invention are:
2-[3-(2,6-Dioxo-1,3-dipropyl-2,3,6,7-tetrahydro-1H-purin-8-yl)-5-methyl-pyrazol-1-yl]-N-phenyl-acetamide;
2-[3-(2,6-Dioxo-1,3-dipropyl-2,3,6,7-tetrahydro-1H-purin-8-yl)-5-methyl-pyrazol-1-yl]-N-(4-iodophenyl)-acetamide;
2-[3-(2,6-Dioxo-1,3-dipropyl-2,3,6,7-tetrahydro-1H-purin-8-yl)-5-methyl-pyrazol-1-yl]-N-(4-bromophenyl)acetamide;
2-[3-(2,6-Dioxo-1,3-dipropyl-2,3,6,7-tetrahydro-1H-purin-8-yl)-5-methyl-pyrazol-1-yl]-N-(4-chlorophenyl)-acetamide;
2-[3-(2,6-Dioxo-1,3-dipropyl-2,3,6,7-tetrahydro-1H-purin-8-yl)-5-methyl-pyrazol-1-yl]-N-(4-fluoro-phenyl)-acetamide;

2-[3-(2,6-Dioxo-1,3-dipropyl-2,3,6,7-tetrahydro-1H-purin-8-yl)-5-methyl-pyrazol-1-yl]-N-(4-methoxyphenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dimethylphenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dimethoxyphenyl)-acetamide;

2-[3-(2,6-Dioxo-1,3-dipropyl-2,3,6,7-tetrahydro-1H-purin-8-yl)-5-ethyl-pyrazol-1-yl]-N-(4-chlorophenyl)acetamide;

2-[3-(2,6-Dioxo-1,3-dipropyl-2,3,6,7-tetrahydro-1H-purin-8-yl)-pyrazol-1-yl]-N-(4-chloro-phenyl)-acetamide;

2-[3-(2,6-Dioxo-1,3-dipropyl-2,3,6,7-tetrahydro-1H-purin-8-yl)-5-methyl-pyrazol-1-yl]-N-(4-dimethylaminophenyl)-acetamide;

2-[3-(2,6-Dioxo-1,3-dipropyl-2,3,6,7-tetrahydro-1H-purin-8-yl)-5-methyl-pyrazol-1-yl]-N-(4-sec-butylphenyl)-acetamide;

2-[3-(2,6-Dioxo-1,3-dipropyl-2,3,6,7-tetrahydro-1H, purin-8-yl)-5-methyl-pyrazol-1-yl]-N (naphthalen-1-yl)-acetamide;

2-[3-(2,6-Dioxo-1,3-dipropyl-2,3,6,7-tetrahydro-1H-purin-8-yl)-5-methyl-pyrazol-1-yl]-N-(3-methoxylphenyl)-acetamide;

2-[3-(2,6-Dioxo-1,3-dipropyl-2,3,6,7-tetrahydro-1H-purin-8-yl)-5-methyl-pyrazol-1-yl]-N-(3-chlorophenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dichlorophenyl)-acetamide;

2-[3-(2,6-Dioxo-1,3-dipropyl-2,3,6,7-tetrahydro-1H-purin-8-yl)-5-methyl-pyrazol-1-yl]-N-p-tolyl-acetamide;

2-[4-Chloro-3-(2,6-dioxo-1,3-dipropyl-2,3,6,7-tetrahydro-1H-purin-8-yl)-5-methyl-pyrazol-1-yl]-N-(4-chlorophenyl)-acetamide;

2-[4-Bromo-3-(2,6-dioxo-1,3-dipropyl-2,3,6,7-tetrahydro-1H-purin-8-yl)-5-methyl-pyrazol-1-yl]-N-(4-chlorophenyl)-acetamide; and 2-[4-Iodo-3-(2,6-dioxo-1,3-dipropyl-2,3,6,7-tetrahydro-1H-purin-8-yl)-5-methyl-pyrazol-1-yl]-N-(4-chlorophenyl)-acetamide;

or a pharmaceutically acceptable salt thereof.

Compounds of formula (I) may be prepared using methods well known in the art, or using modifications thereof, e.g., as outlined herein in Scheme 1.

Scheme 1:

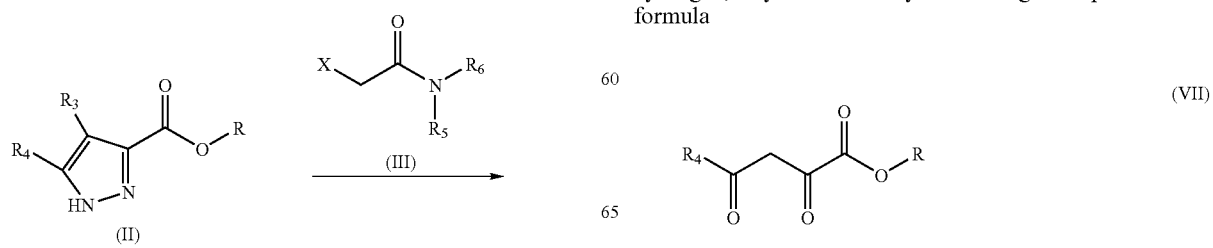

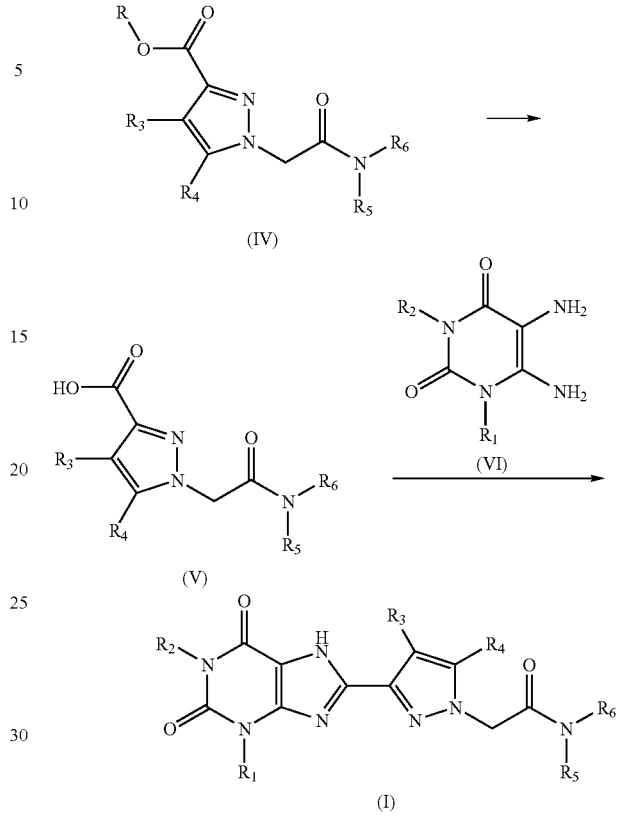

As exemplified in Scheme 1, compounds of formula (I), wherein $R_1$, $R_2$, $R_3$, $R_4$, $R_5$ and $R_6$ have a meaning as defined herein above, may be prepared starting from compounds of formula (II), wherein $R_3$ and $R_4$ have a meaning as defined herein above, and R represents lower alkyl, preferably methyl or ethyl, i.e., a compound of formula (II) may be converted to a compound of formula (IV), wherein R, $R_3$, $R_4$, $R_5$ and $R_6$ have a meaning as defined herein above, by treatment with an alkylating agent of formula (III), wherein $R_5$ and $R_6$ have a meaning as defined herein above, and X represents a leaving group such as chloride, bromide, iodide, mesylate or tosylate. Preferably, the alkylation is carried out at room temperature (RT) in an organic solvent such as a lower alcohol, e.g., methanol (MeOH) or ethanol (EtOH), in the presence of a base such as a metal alkoxide, e.g., sodium methoxide or sodium ethoxide.

Compounds of formula (II), wherein R, $R_3$ and $R_4$ have a meaning as defined herein above, are known, or if they are novel they may be prepared using methods well known in the art, or modifications thereof.

For example, a compound of formula (II), wherein $R_3$ is hydrogen, may be obtained by condensing a compound of the formula

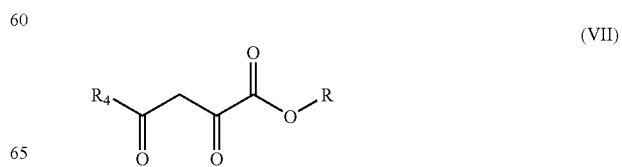

wherein R and $R_4$ have a meaning as defined herein above, with salts of hydrazine in a polar organic solvent such as a lower alcohol, e.g., EtOH, at an elevated temperature, preferably, at or near the boiling point of the solvent.

Furthermore, a compound of formula (II), wherein $R_3$ is hydrogen, may be converted to a corresponding compound of formula (II), wherein $R_3$ is halogen, by treatment with a halogenating agent such as N-halosuccinimide, e.g., N-chlorosuccinimide, N-bromosuccinimide and N-iodosuccinimide, in the presence of a suitable organic solvent, e.g., N,N-dimethylformamide (DMF). Preferably, the reaction is conducted at a temperature ranging from about 0° C. to RT.

Likewise, compounds of formula (III), wherein X, $R_5$ and $R_6$ have a meaning as defined herein above, are known, or if they are novel they may be prepared as described herein in the illustrative Examples, or using methods well known in the art, or modifications thereof.

Hydrolysis of a compound of formula (IV), wherein R, $R_3$, $R_4$, $R_5$ and $R_6$ have a meaning as defined herein above, then afford a compound of formula (V), wherein $R_3$, $R_4$, $R_5$ and $R_6$ have a meaning as defined herein above, e.g., a compound of formula (IV), wherein R is lower alkyl such as methyl or ethyl, may be treated with an aqueous base such as sodium hydroxide (NaOH) or potassium hydroxide (KOH) in an organic solvent such as tetrahydrofuran (THF) or dioxane, preferably dioxane. The hydrolysis step is preferably conducted at RT.

A resulting compound of formula (V), wherein $R_3$, $R_4$, $R_5$ and $R_6$ have a meaning as defined herein above, may then be coupled with a 1,3-disubstituted-5,6-diaminouracil of formula (VI), wherein $R_1$ and $R_2$ have a meaning as defined herein above, in the presence of a coupling agent such as such as 3-ethyl-1-(3-dimethylaminopropyl)-3-ethylcarbodiimide hydrochloride (EDCl) or 1,3-dicyclohexylcarbodiimide (DCC) and an organic solvent such as a lower alcohol, preferably, MeOH or EtOH, to afford an intermediate amide derivative(s) which upon subsequent treatment with an aqueous base such as NaOH or KOH in an organic solvent such as a lower alcohol, preferably MeOH, cyclizes to afford a compound of formula (I), wherein $R_1$, $R_2$, $R_3$, $R_4$, $R_5$ and $R_6$ have a meaning as defined herein above. Preferably, the coupling reaction is carried at room temperature (RT), and the cyclization step at a temperature ranging from about 50 to about 80° C.

The processes described herein above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc, N.Y. (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts.

Compounds of the invention and intermediates can also be converted into each other according to methods generally known per se.

The present invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers, racemates or mixtures thereof. The aforesaid possible isomers or mixtures thereof are within the purview of the present invention.

Any resulting mixtures of isomers can be separated on the basis of the physicochemical differences of the constituents, into the pure geometric or optical isomers, diastereomers, for example, by fractional crystallization and/or chromatography, e.g., by high pressure liquid chromatography (HPLC) using a chiral adsorbent.

Finally, compounds of the invention are either obtained in the free form, or in a salt form thereof, preferably, in a pharmaceutically acceptable salt form thereof.

In particular, compounds of the invention which contain basic groups may be converted into acid addition salts, especially pharmaceutically acceptable acid addition salts. These are formed, e.g., with inorganic acids, such as mineral acids, e.g., sulfuric acid, phosphoric or hydrohalic acid, or with organic carboxylic acids, such as $C_1$-$C_4$ alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $C_1$-$C_4$ alkylsulfonic acids, e.g., methanesulfonic acid; or arylsulfonic acids which are unsubstituted or substituted (for example by halogen). Preferred are salts formed with hydrochloric acid, maleic acid and methanesulfonic acid. Salts may be formed using conventional methods, advantageously in the presence of an ethereal or alcoholic solvent, such as a lower alkohol. From the solutions of the latter, the salts may be precipitated with ethers, e.g., with diethyl ether or petroleum ether. Resulting salts may be converted into the free compounds by treatment with a suitable base, e.g., sodium hydroxide. These or other salts can also be used for the purification of the compounds obtained.

In view of the close relationship between the free compounds and the compounds in the form of their salts, whenever a compound is referred to a corresponding salt is also intended, provided such is possible or appropriate under the circumstances.

The compounds, including their salts, can also be obtained in the form of their hydrates, or include other solvents used for their crystallization.

Furthermore, compounds of formula (I) may be obtained labeled with any suitable radiolabel. Examples of suitable radiolabels include tritium ($^3$H) and carbon radioisotopes, e.g., $^{14}$C, but any substantially non-toxic radiolabel commonly used in pharmacokinetic studies may be employed. Means for incorporating radiolabels onto organic compounds are well known to those of ordinary skill in the art.

For example, 1,3-disubstituted-5,6-diaminouracils of formula (VI) may be obtained containing a suitable radiolabel, e.g., 1,3-disubstituted-5,6-diaminouracils of formula (VI) wherein $R_1$ and $R_2$ contain one or more sites of unsaturation are easily accessible. The unsaturated carbon-carbon double or triple bond(s) may then be reacted with tritium in the presence a suitable catalyst, e.g., palladium on charcoal or other known hydrogenation catalysts. Using the radiolabelled diaminouracil and following the methods of synthesis described herein above will then result in the corresponding radiolabelled compounds of formula (I).

It has been established in the art, that $^3$H and $^{14}$C labeled compounds have binding affinity to the adenosine $A_1$, $A_{2A}$, $A_{2B}$, and $A_3$ receptor subtypes comparable to that of corresponding non-labeled forms and, thus, radiolabelled compounds of formula (I) may be employed as radioligands for studying biological activity associated with the adenosine receptors, in particular, the adenosine $A_{2B}$ receptor.

As described herein above, the compounds of the present invention are adenosine $A_{2B}$ receptor antagonists. Thus, the present invention provides a method for the modulation of the adenosine $A_{2B}$ receptor activity in mammals which method comprises administering to a mammal in need thereof a therapeutically effective amount of a compound of formula (I).

Furthermore, compounds of formula (I) may be employed for the treatment of conditions mediated by the adenosine $A_{2B}$ receptors. Accordingly, such compounds may be employed therapeutically for the treatment of chronic and acute inflammatory diseases involving degranulation of mast cells, e.g., asthma, allergic rhinitis and allergic dermatitis; impaired sensitivity to insulin, e.g., type 2 diabetes, non-insulin dependent diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

In other words, the present invention provides a method for the treatment of conditions mediated by the adenosine $A_{2B}$ receptor, which comprises administering to a mammal in need thereof a therapeutically effective amount of a compound of the present invention.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals. The preferred mammals are humans.

Preferably, the methods of the present invention are directed to the treatment of asthma and diabetes.

Likewise, the present invention provides a method as defined above comprising co-administration, e.g. concomitantly or in sequence, of a therapeutically effective amount of a compound of formula (I), or a pharmaceutically acceptable salt thereof, and a second drug substance, said second drug substance being an anti-inflammatory agent, an anti-diabetic agent or an anti-hypertensive agents, e.g., as indicated herein below.

The present invention further provides pharmaceutical compositions comprising a therapeutically effective amount of a compound of the present invention, alone or in combination with one or more pharmaceutically acceptable carriers.

The pharmaceutical compositions according to the invention are those suitable for enteral, such as oral or rectal, transdermal and parenteral administration to mammals, including man, for the treatment of conditions mediated by the adenosine $A_{2B}$ receptor. Such conditions include, but are not limited to, chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

Thus, the compounds of the present invention may be employed in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively.

Generally, the concentration of the compound(s) of the present invention in a liquid composition, such as a lotion, will be from about 0.01-25 wt-%, preferably from about 0.1-10 wt-%. The concentration in a semi-solid or a solid composition such as a gel or a powder will be about 0.1-5 wt-%, preferably about 0.5-2.5 wt %.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

When used in the treatment of treatment for ischemic injury to retinal vessels the compounds of the present invention are preferably formulated in eye drops suitable for topical application.

The compounds of the invention may be administered by inhalation from an inhaler, insufflator, atomizer or pressurized pack or other means of delivering an aerosol spray. Pressurized packs may use a suitable propellant such as carbon dioxide or other suitable gas. In the case of a pressurized aerosol, the dosage unit may be determined by providing a value to deliver a metered amount. The inhalers, insufflators, and atomizers are fully described in pharmaceutical reference books such as Remington's Pharmaceutical Sciences 18th edition (1990) Mack Publishing Co., Easton, Pa.

The amount of a compound of the present invention required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day. For example, a dosage may be from 0.002 mg/kg to about 10 mg/kg of body weight per day, preferably in the range of 0.01 mg/kg/day to 1 mg/kg/day, and most preferably in the range of 0.1 mg/kg/day to 5 mg/kg/day.

The compound is conveniently administered in unit dosage form, e.g., containing 5 to 1000 µg, conveniently 10 to 750 µg, most conveniently, 50 to 500 µg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. Dosages above or below the range cited herein above are within the scope of the present invention and may be administered to the individual patient if desired and necessary.

Accordingly, the present invention provides pharmaceutical compositions as described above for the treatment of conditions mediated by the adenosine $A_{2B}$ receptor including chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-inflammatory agents, such as anticholinergic or antimuscarinic agents; steroids; $LTB_4$ (leukotriene $B_4$) antagonists; dopamine receptor agonists; $PDE_4$ (phosphodiesterase 4) inhibitors; and beta-2 adrenergic receptor agonists;

b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguamides; alpha-glucosidase inhibitors; GLP-1 (glucagon like peptide-1), GLP-1 analogs and GLP-1 mimetics; modulators of PPARs (peroxisome proliferator-activated receptors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

c) anti-hypertensive agents, such as loop diuretics; angiotensin converting enzyme (ACE) inhibitors; inhibitors of the Na-K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA) reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

As described above, a compound of the present invention may be administered either simultaneously, before or after the other active ingredient, either separately by the same or different route of administration or together in the same pharmaceutical formulation.

Accordingly, the present invention provides pharmaceutical compositions comprising a therapeutically effective amount of a compound of the invention in combination with a therapeutically effective amount of another therapeutic agent, preferably selected from anti-inflammatory agents, anti-diabetic agents, anti-hypertensive agents and anti-dyslipidemic agents.

Since the present invention has an aspect that relates to treatment with a combination of compounds which may be co-administered separately, the invention also relates to combining separate pharmaceutical compositions in kit form. The kit comprises two separate pharmaceutical compositions: (1) a composition comprising a compound of formula (I), or a pharmaceutically acceptable salt thereof, plus a pharmaceutically acceptable carrier or diluent; and (2) a composition comprising an anti-inflammatory agent, an anti-diabetic agent, an anti-hypertensive agent or an anti-dyslipidemic agent, or a pharmaceutically acceptable salt thereof, plus a pharmaceutically acceptable carrier or diluent. The amounts of (1) and (2) are such that, when co-administered separately, a beneficial therapeutic effect(s) is achieved. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising a pharmaceutical composition (1), and the second (or more) tablet(s) comprising a pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the present invention a kit therefore comprises:

(1) a therapeutically effective amount of a composition comprising a compound of formula (I), or a pharmaceutically acceptable salt thereof, and a pharmaceutically acceptable carrier or diluent, in a first dosage form;

(2) a composition comprising an anti-inflammatory agent, an anti-diabetic agent, an anti-hypertensive agent or an anti-dyslipidemic agent, or a pharmaceutically acceptable salt thereof in an amount such that, following administration, a beneficial therapeutic effect(s) is achieved, and a pharmaceutically acceptable carrier or diluent, in a second dosage form; and (3) a container for containing said first and second dosage forms.

The present invention further relates to pharmaceutical compositions as described above for use as a medicament.

The present invention further relates to use of pharmaceutical compositions or combinations as described above for the preparation of a medicament for the treatment of conditions mediated by the adenosine $A_{2B}$ receptor including chronic and acute inflammatory diseases involving degranulation of mast cells, e.g., asthma, allergic rhinitis and allergic dermatitis; impaired sensitivity to insulin, e.g., type 2 diabetes, pre-diabetic state, and impaired glucose tolerance; diseases in which angiogenesis is a key component of pathogenesis, e.g., solid tumors and angiogenic retinopathies; apnea of preterm infants; myocardial reperfusion injury; inflammatory bowel disease; autoimmune diseases, such as rheumatoid arthritis, multiple sclerosis, and lupus erythematosis; diseases involving microvascular abnormalities of the retina that are mediated by adenosine $A_{2B}$ receptors, e.g., retinopathy of prematurity, macular degeneration, and diabetic retinopathy; and cardiac diseases including hyperplasia consequent to hypertension, arteriosclerosis, and heart attack.

Thus, the present invention also relates to a compound of formula (I) for use as a medicament, to the use of a compound of formula (I) for the preparation of a pharmaceutical composition for the treatment of conditions mediated by the adenosine $A_{2B}$ receptor, and to a pharmaceutical composition for use in conditions mediated by the adenosine $A_{2B}$ receptor comprising a compound of formula (I), or a pharmaceutically acceptable salt thereof, in association with a pharmaceutically acceptable diluent or carrier therefore.

Finally, the present invention provides a method or use which comprises administering a therapeutically effective amount of a combination of a compound of formula (I) and an anti-inflammatory agent, an anti-diabetic agent, an anti-hypertensive agent or an anti-dyslipidemic agent.

Ultimately, the present invention provides a method or use which comprises administering a compound of formula (I) in the form of a pharmaceutical composition as described herein.

The above-cited properties are demonstrable in vitro and in vivo tests using advantageously mammals, e.g., mice, rats, dogs, sheep, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.001 mg/kg and 1000 mg/kg, preferably between about 0.01 mg/kg and 100 mg/kg, more preferably between about 0.1 mg/kg and 10 mg/kg.

The activity of compounds according to the invention may be assessed using methods well-described in the art, e.g., as described herein below:

CHO membranes Preparation

The human adenosine receptors have been transfected in CHO cells according with the method previously described by Klotz et al. (*Naunyn-Schmied. Arch Pharm.* 1998, 357: 1-9). Briefly, the cells are grown adherently and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G418, 0.2 mg/ml) at 37° C. in 5% $CO_2$/95% air. For membrane preparation the culture medium is removed and the cells are washed with phosphate-buffered saline and scraped off T75 flasks in ice-cold hypo tonic buffer (5 mM Tris HCl, 1 mM EDTA, pH 7.4). The cell suspension is homogenized with Polytron, the homogenate is spun for 10 min at 1000×g and the supernatant is then centrifuged for 30 min at 100,000×g. The membrane pellet is suspended in 50 mM Tris HCl buffer (pH 7.4) for $A_1$ adenosine receptors, in 50 mM Tris HCl, 10 mM $MgCl_2$ (pH 7.4) for $A_{2A}$ adenosine receptors, in 50 mM Tris HCl, 10 mM $MgCl_2$, 1 mM EDTA (pH 7.4) for $A_{2B}$ and $A_3$ adenosine receptors.

Human Cloned $A_1$, $A_{2A}$, $A_{2B}$ and $A_3$ Adenosine Receptor Binding Assay All new synthesized compounds have been tested to evaluate their affinity to human $A_1$, $A_{2A}$, $A_{2B}$ and $A_3$ adenosine receptors. Displacement experiments of [$^3$H]-DPCPX to CHO cells transfected with the human recombinant $A_1$ adenosine receptors are performed for 120 min at 25° C. incubating diluted membranes (50 µg of protein/assay) and at least 6-8 different concentrations of examined antagonists (Varani et al., *Mol. Pharmacol.*, 2000, 57: 968-975). Non-specific binding is determined in the presence of 10 µM of CHA and this is always ≦10% of the total binding. Binding of [$^3$H]-ZM 241385 to CHO cells transfected with the human recombinant $A_{2A}$ adenosine receptors is performed using a suspension of membranes (50 μg of protein/assay) and at least 6-8 different concentrations of studied antagonists for an incubation time of 60 min at 4° C. Non-specific binding is determined in the presence of 1 μM ZM 241385 and is about 20% of total binding. Competition binding experiments of [$^3$H]-MRE 2029F20 to CHO cells transfected with the human recombinant A$_{2B}$ adenosine receptors are carried out incubating for 120 min at 4° C. diluted membranes (50 μg of protein/assay) and at least 6-8 different concentrations of examined compounds. Non-specific binding is defined as binding in the presence of 1 μM MRE 3029F20 and is about 25% of total binding. Competition binding experiments of [$^3$H]-MRE 3008F20 to CHO cells transfected with the human recombinant A$_3$ adenosine receptors[5] are carried out incubating for 120 min at 4° C. diluted membranes (50 μg of protein/assay) and at least 6-8 different concentrations of examined ligands. Non-specific binding is defined as binding in the presence of 1 μM MRE 3008F20 and is about 25% of total binding. Bound and free radioactivity are separated by filtering the assay mixture through Whatman GF/B glass fiber filters using a Micro-Mate 196 cell harvester (Packard Instrument Co.). The filter bound radioactivity is counted on a Top Count (efficiency 57%) with Micro-Scint 20.

Measurement of Cyclic AMP Levels in CHO Cells Transfected with Human A$_{2B}$ Adenosine Receptors CHO cells transfected with human A$_{2B}$ adenosine receptors are washed with phosphate-buffered saline, diluted trypsine and centrifuged for 10 min at 200 g. The pellet containing the CHO cells (1×10$^6$ cells/assay) is suspended in 0.5 mL of incubation mixture: NaCl 150 mM, KCl 2.7 mM, NaH$_2$PO$_4$ 0.37 mM, MgSO$_4$ 1 mM, CaCl$_2$ 1 mM, Hepes 5 mM, MgCl$_2$ 10 mM, glucose 5 mM, pH 7.4 at 37° C. Then 2.0 IU/mL adenosine deaminase and 0.5 mM 4-(3-butoxy-4-methoxybenzyl)-2-imidazolidinone (Ro 20-1724) as phosphodiesterase inhibitor are added and preincubated for 10 min a shaking bath at 37° C. The potency of antagonists studied are determined by antagonism of NECA (100 nM)-induced stimulation of cyclic AMP levels. The reaction is terminated by the addition of cold 6% thrichloroacetic acid (TCA). The TCA suspension is centrifuged at 2000 g for 10 min at 4° C. and the supernatant is extracted four times with water saturated diethyl ether. The final aqueous solution is tested for cyclic AMP levels by a competition protein binding assay. Samples of cyclic AMP standard (0-10 μmol) are added to each test tube containing the incubation buffer (trizma base 0.1 M, aminophylline 8.0 mM, 2-mercaptoethanol 6.0 mM (pH 7.4) and [$^3$H]cyclic AMP in a total volume of 0.5 mL. The binding protein previously prepared from beef adrenals, is added to the samples previously incubated at 4° C. for 150 min, and after the addition of charcoal are centrifuged at 2000 g for 10 min. The clear supernatant is counted with 4 mL of Atomlight liquid scintillator and counted in a Tri Carb Packard 2500 TR scintillation counter.

Data Analysis

The protein concentration is determined according to a Bio-Rad method (Bradford, Anal Biochem. 1976, 72: 248-254) with bovine albumin as a standard reference. Inhibitory binding constant, K$_i$, values are calculated from those of IC$_{50}$ according to Cheng & Prusoff equation (*Biochem. Pharmacol* 1973, 22: 3099-3108):

$$K_i = IC_{50}/(1+[C^*]/K_D^*)$$

where [C*] is the concentration of the radioligand and K$_D$* its dissociation constant. A weighted non linear least-squares curve fitting program LIGAND (Munson et al., *Anal. Biochem* 1980, 107: 220-239) is used for computer analysis of inhibition experiments Data are expressed as geometric mean with 95% confidence limits in parentheses.

Examples of Animal Models

The effectiveness of a compound of the present invention in inhibiting inflammatory conditions, e.g., inflammatory airways diseases, may be demonstrated in an appropriate animal model, e.g., a mouse or rat model, of airways inflammation or other inflammatory conditions, e.g., as described by Szarka et al., *J. Immunol. Methods* 1997, 202: 49-57; Renzi et al., *Am. Rev. Respir. Dis.* 1993, 148: 932-939; Tsuyuki et al., *J. Clin Invest.* 1995, 96: 2924-2931; and Cemadas et al., *Am. J. Respir. Cell Mol. Biol.* 1999, 20:1-8. Preferably, the in vivo efficacy of a compound of the present invention is examined in sheep which are naturally sensitive to the allergen *Ascaris suum*, e.g., as described by Abraham et al., *Am. J. Respir. Crit. Care. Med.* 2000, 162: 603-611; Fath et al., *J. Biol. Chem.* 1998, 273: 13563-13569; and Fujimoto et al., *Eur. Respir. J.* 1996, 9: 2044-2049.

The in vivo efficacy of a compound of the present invention for treating cardiac diseases may be evaluated in animal models well known in the art, e.g., by employing an apolipoprotein E knockout mouse model which has become one of the primary models for atherosclerosis (*Arterioscier. Thromb. Vasc. Biol.* 2004, 24: 1006-1014; *Trends Cardiovasc. Med.* 2004, 14: 187-190). The studies may be performed as described by Johnson et al. in *Circulation* 2005, 111: 1422-1430, or using modifications thereof.

The glucose and insulin lowering activity of a compound of the present invention in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day one tail blood samples are taken at 8:00 am and plasma glucose levels are determined. The animals are randomly assigned to the control and compound groups. The means of plasma glucose values of the groups are matched. Animals are then orally dosed with vehicle (e.g., 0.5% carboxymethyl-cellulose with 0.2% Tween-80) or a test compound in vehicle, e.g., at 30 mg/kg. The mice are dosed daily for a total of 3 days. On day 4 basal blood samples are taken. The plasma samples are analyzed for glucose concentrations using, e.g., a YSI2700 Dual Channel Biochemistry Analyzer (Yellow Springs Instrument Co., Yellow Springs, Ohio) and insulin concentrations using an ELISA assay.

Illustrative of the invention, the compound of Example 4 demonstrates an IC$_{50}$ value of about 43 nM in a functional assay measuring the cAMP level in CHO cells expressing the human adenosine A$_{2B}$ receptor. Additional binding and functional data for the illustrative Examples of the present invention are presented in Table 1.

TABLE 1

| Example No. | $K_i$ (nM) hA$_1$[a] | hA$_{2A}$[b] | hA$_3$[c] | hA$_{2B}$[d] | IC$_{50}$ (nM) hA$_{2B}$[e] |
|---|---|---|---|---|---|
| 1  | 350 (275-482) | >1000  | >1000  | 15 (10-21)    | 58 (45-74)    |
| 2  | >1000         | >1000  | >1000  | 28 (18-43)    | 115 (84-159)  |
| 3  | >1000         | >1000  | >1000) | 35 (27-45)    | 156 (123198)  |
| 4  | >1000)        | >1000  | >1000  | 7.0 (5 34-9 06) | 43 (31-60)  |
| 5  | 500 (420-595) | >1000  | >1000  | 14 (10-20)    | 68 (51-91)    |
| 6  | >1000         | >1000  | >1000  | 12 (8-18)     | 61 (44-84)    |
| 7  | >1000         | >1000  | >1000  | 48 (35-65)    | 200 (182-219) |
| 8  | >1000         | >1000  | >1000  | 60 (44-82)    | 222 (203-242) |
| 9  | >1000         | >1000  | >1000  | >1000         | >1000         |
| 10 | 140 (123-159) | >1000  | >1000  | 20 (15-26)    | 80 (63-100)   |
| 11 | >1000         | >1000) | >1000  | >1000         | >1000         |
| 12 | >1000         | >1000) | >1000  | >1000         | >1000         |
| 13 | >1000         | >1000  | >1000  | >1000         | >1000         |
| 14 | 480 (444-518) | >1000  | >1000  | 65 (56-75)    | 266 (216-327) |
| 15 | 675 (569-800) | >1000  | >1000  | 28 (19-41)    | 106 (81-139)  |
| 16 | >1000         | >1000  | >1000  | 40 (25-66)    | 188 (166-213) |
| 17 | >1000         | >1000  | >1000  | 56 (45-70)    | 212 (162-277) |
| 18 | >1000         | >1000  | >1000  | 222 (181-273) | >1000         |
| 19 | >1000         | >1000  | >1000  | 250 (205-306) | >1000         |
| 20 | >1000         | >1000  | >1000  | >1000         | >1000         |

[a]Displacement of specific [$^3$H]DPCPX binding at human A$_1$ receptors expressed in CHO cells (n = 3-6)
[b]Displacement of specific [$^3$H]ZM241385 binding at human A$_{2A}$ receptors expressed in CHO cells (n = 3-6)
[c]Displacement of specific [$^3$H]MRE2029F20 binding at human A$_{2B}$ receptors expressed in HEK293 cells (n = 3-6).
[d]Displacement of specific [$^3$H]MRE3008F20 binding at human A$_3$ receptors expressed in CHO cells (n = 3-6).
[e]cAMP assays have been performed in CHO cells expressing human A$_{2B}$ adenosine receptors
Binding and functional data are expressed as K$_j$ (nM) and IC$_{50}$ (nM), respectively.
Experimental data are expressed as geometric means with 95% confidence limits The Examples disclosed herein are intended to illustrate the invention and are not to be construed as being limitations thereon. If not mentioned otherwise, all evaporations are performed under reduced pressure, preferably between about 10 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

EXAMPLE 1

2-[3-(2,6-Dioxo-1,3-dipropyl-2,3,6,7-tetrahydro-1H-purin-8-yl)-5-methyl-pyrazol-1-yl]-N-phenyl-acetamide

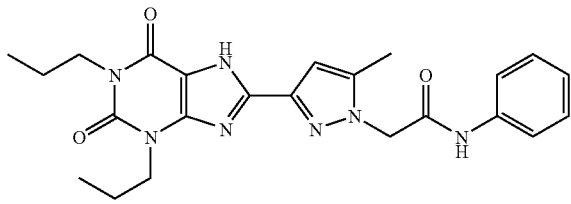

A. 2-Bromo-N-phenylacetamide

A solution of aniline (0.016 mol) in 40 mL of dichloromethane is cooled on ice, and 1.0 equivalent of bromoacetyl bromide in 3 mL of dichloromethane is added dropwise, followed by 0.019 mol of triethylamine (TEA). The solution turns dark and a precipate forms, as the reaction mixture is warmed to RT over 3 h. The mixture is concentrated and taken up in ethyl acetate (EtOAc) and washed three times with water. The organic phase is dried over anhydrous sodium sulphate (Na$_2$SO$_4$), filtered and concentrated. The residue is purified by crystallization from EtOAc to afford 2-bromo-N-phenylacetamide: m.p. 131-135° C.; $^1$H-NMR (CDCl$_3$) δ 4.01 (s, 2H), 7.18 (m, 1H), 7.36 (m, 2H), 7.54 (2H), 8.09 (s, 1H).

B. 5-Methyl-1-phenylcarbamoylmethyl-1H-pyrazole-3-carboxylic acid ethyl ester To a magnetically stirred mixture of ethyl 5-methyl-1H-pyrazole-3-carboxylate (0.02 mol) and sodium ethoxide (0.22 mol) in ethanol (20 mL) is added the title A compound, 2-bromo-N-phenyl-acetamide (0.02 mol). The resulting suspension is stirred at RT for 3 h. After concentration in vacuo, EtOAc is added and the resulting solution is washed twice with water and dried over anhydrous Na$_2$SO$_4$. After filtration and concentration, the residue is purified by flash chromatography (ethyl acetate/hexane) to afford 5-methyl-1-phenylcarbamoyl-methyl-1H-pyrazole-3-carboxylic acid ethyl ester: m.p. 139-140° C.; $^1$H-NMR (DMSO-d$_6$) δ 1.26-1.29 (t, 3H J=72 Hz), 2.28 (s, 3H), 4.23-4.25 (q, 2H J=72 Hz), δ 06 (s, 2H), δ 6.56 (s, 1H), 7.07 (m, 1H), 7.32 (m, 2H), 7.57 (m, 2H), 10.41 (s, 1H).

C. 5-Methyl-1-phenylcarbamoylmethyl-1H-pyrazole-3-carboxylic acid

To a magnetically stirred mixture of the title B compound, 5-methyl-1-phenylcarbamoyl-methyl-1H-pyrazole-3-carboxylic acid ethyl ester (3.0 mmol), in dioxane (50 mL) is added aqueous 2 N KOH (5 mL) and the resulting mixture is stirred at RT for 3 h to give a solution. After concentration in vacuo, the residue is cooled and acidified with a 10% HCl solution to precipitate 5-methyl-1-phenylcarbamoylmethyl-1H-pyrazole-3-carboxylic acid as a white solid: m.p. 273-275° C.; $^1$H-NMR (DMSO-d) δ 2.28 (s, 3H), δ 06 (s, 2H), δ 56 (s, 1H), 7.07 (m, 1H), 7.32 (m, 2H), 7.57 (m, 2H), 10.41 (s, 1H), 12.50 (s, 1H).

D. 2-[3-(2,6-Dioxo-1,3-dipropyl-2,3,6,7-tetrahydro-1H-purin-8-yl)-5-methyl-pyrazol-1-yl]-N-phenyl-acetamide To a solution of 1,3-dipropyl-5,6-diaminouracil (2.20 mmol), in MeOH (10 mL), is added an equimolar amount of the title C compound, 5-methyl-1-phenylcarbamoylmethyl-1H-pyrazole-3-carboxylic acid, and EDCl (2.21 mmol). The reaction mixture is stirred at RT for 4-5 h while being monitored by TLC. The solvent is concentrated in vacuo and the amide intermediate is precipitated by the addition of water. After filtration, the solid is dissolved in MeOH (10 mL) and aqueous NaOH (2.5 N, 15 mL) and the mixture is stirred at 50-60° C. for 1 h. The MeOH is distilled off, and the residue is taken up in H$_2$O and acidified with HCl to pH 4-5. The precipitate is collected by filtration, washed with water, and purified by flash chromatography (ethyl acetate-petroleum ether) to afford 2-[3-(2,6-dioxo-1,3-dipropyl-2,3,6,7-tetrahydro-1H-purin-8-yl)-5-methyl-pyrazol-1-yl]-N-phenyl-acetamide: m.p. 255-257° C.; $^1$H-NMR (DMSO-d$_6$) δ 0.87 (m, 6H), 1.56 (q, 2H), 1.70 (q, 2H), 2.32 (s, 3H), 3.84 (m, 2H), 3.98 (m, 2H), δ0.08 (s, 2H), 6.74 (s, 1H), 7.08 (m, 1H), 7.33 (m, 2H), 7.59 (m, 2H), 10.41 (s, 1H), 13.85 (s, 1H).

EXAMPLE 2

2-[3-(2,6-Dioxo-1,3-dipropyl-2,3,6,7-tetrahydro-1H-purin-8-yl)-5-methyl-pyrazol-1-yl]-N-(4-iodophenyl)-acetamide

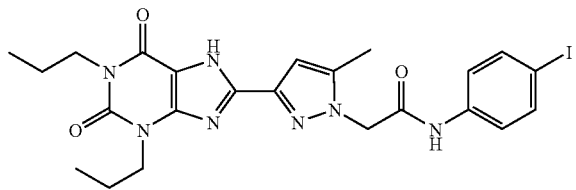

The title compound is prepared analogously to Example 1: m.p 286-289° C.; $^1$H-NMR (DMSO-d$_6$) δ 0.87 (m, 6H), 1.56 (q, 2H), 1.71 (q, 2H), 2.30 (s, 3H), 3.84 (t, 2H), 3.97 (t, 2H), 5.07 (s, 2H), 6.74 (s, 1H), 7.42 (d, 2H J=8.8 Hz), 7.66 (d, 2H J=8.8 Hz), 10.52 (s, 1H), 13.69 (s, 1H).

EXAMPLE 3

2-[3-(2,6-Dioxo-1,3-dipropyl-2,3,6,7-tetrahydro-1H-purin-8-yl)-5-methyl-pyrazol-1-yl]-N-(4-bromophenyl)acetamide

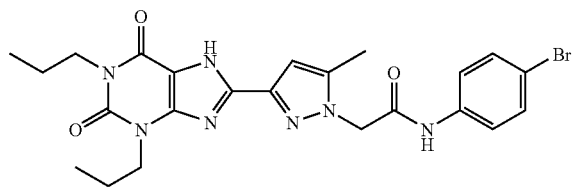

The title compound is prepared analogously to Example 1: m.p. 270-273° C.; $^1$H-NMR (DMSO-d$_6$) δ 0.87 (m, 6H), 1.56 (q, 2H), 1.70 (q, 2H), 2.31 (s, 3H), 3.85 (m, 2H), 3.98 (m, 2H), 5.08 (s, 2H), 6.75 (s, 1H), 7.51 (d, 2H J=8.0 Hz), 7.57 (d, 2H J=80 Hz), 10.56 (s, 1H), 13.68 (s, 1H).

EXAMPLE 4

2-[3-(2,6-Dioxo-1,3-dipropyl-2,3,6,7-tetrahydro-1H-purin-8-yl)-5-methyl-pyrazol-1-yl]-N-(4-chlorophenyl)-acetamide

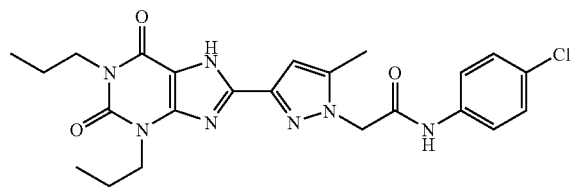

The title compound is prepared analogously to Example 1: m.p. 261-265° C.; $^1$H-NMR (DMSO-d$_6$) δ 0.87 (m, 6H), 1.56 (q, 2H), 1.70 (q, 2H), 2.31 (s, 3H), 3.82 (m, 2H), 3.95 (m, 2H), 5.07 (s, 2H), δ 7.73 (s, 1H), 7.37 (d, 2H J=8.2 Hz), 7.60 (d, 2H J=8.2 Hz), 10.55 (s, 1H), 13.68 (s, 1H).

EXAMPLE 5

2-[3-(2,6-Dioxo-1,3-dipropyl-2,3,6,7-tetrahydro-1H-purin-8-yl)-5-methyl-pyrazol-1-yl]-N-(4-fluoro-phenyl)-acetamide

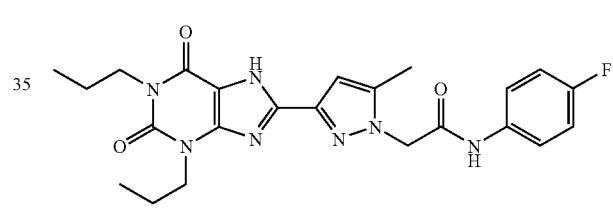

The title compound is prepared analogously to Example 1: m.p. 205-207° C.; $^1$H-NMR (DMSO-d$_6$) δ 0.87 (m, 6H), 1.56 (q, 2H), 1.70 (q, 2H), 2.31 (s, 3H), 3.84 (t, 2H), 3.97 (t, 2H), 5.07 (s, 2H), 6.74 (s, 1H), 7.17 (d, 2H J=8.8 Hz), 7.61 (d, 2H J=8.8 Hz), 10.48 (s, 1H), 13.80 (s, 1H).

EXAMPLE 6

2-[3-(2,6-Dioxo-1,3-dipropyl-2,3,6,7-tetrahydro-1H-purin-8-yl)-5-methyl-pyrazol-1-yl]-N-(4-methoxyphenyl)-acetamide

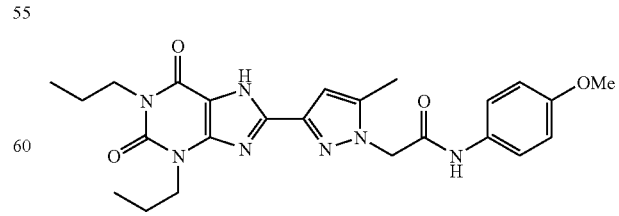

The title compound is prepared analogously to Example 1: m.p. 293-296° C.; $^1$H-NMR (DMSO-d$_6$) δ 0.87 (m, 6H), 1.56 (q, 2H), 1.70 (q, 2H), 2.31 (s, 3H), 3.71 (s, 3H), 3.84 (t, 2H), 3.97 (t, 3H), 5.03 (s, 2H), 6.72 (s, 1H), 7.90 (d, 2H J=8.2 Hz), 7.49 (d, 2H J=8.2 Hz), 10.28 (s, 1H), 13.80 (s, 1H).

EXAMPLE 7

2-[3-(2,6-Dioxo-1,3-dipropyl-2,3,6,7-tetrahydro-1H-purin-8-yl)-5-methyl-pyrazol-1-yl]-N-(3,4-dimethylphenyl)-acetamide

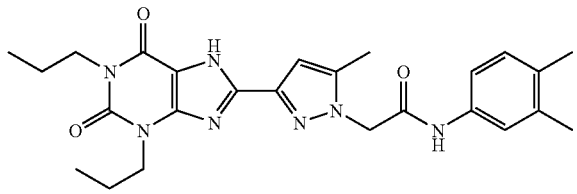

The title compound is prepared analogously to Example 1: m.p. 261-265° C.; $^1$H-NMR (DMSO-d$_6$) δ 0.87 (m, 6H), 1.56 (q, 2H), 1.70 (q, 2H), 2.17 (m, 6H), 2.31 (s, 3H), 3.84 (t, 2H), 3.97 (t, 2H), δ 5.03 (s, 2H), 6.70 (s, 1H), 7.06 (d, 1H), 7.29 (d, 1H), 7.37 (s, 1H), 10.24 (s, 1H), 13.80 (s, 1H).

EXAMPLE 8

2-[3-(2,6-Dioxo-1,3-dipropyl-2,3,6,7-tetrahydro-1H-purin-8-yl)-5-methyl-pyrazol-1-yl]-N-(3,4-dimethoxyphenyl)-acetamide

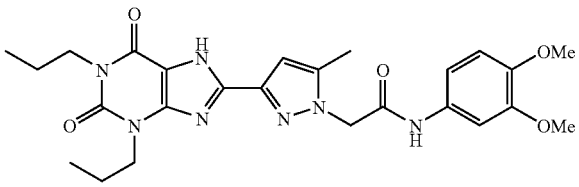

The title compound is prepared analogously to Example 1: m.p. 285-290° C.; $^1$H-NMR (DMSO-d$_6$) δ 0.88 (m, 6H), 1.57 (q, 2H), 1.70 (q, 2H), 2.32 (s, 3H), 3.71 (s, 6H), 3.84 (t, 2H), 3.88 (t, 2H), δ 5.03 (s, 2H), δ 6.73 (s, 1H), 6.90 (d, 1H), 7.05 (d, 1H), 7.32 (s, 1H), 10.29 (s, 1H), 13.88 (s, 1H).

EXAMPLE 9

2-[3-(2,6-Dioxo-1,3-dipropyl-2,3,6,7-tetrahydro-1H-purin-8-yl)-6-ethyl-pyrazol-1-yl]-N-(4-chlorophenyl) acetamide

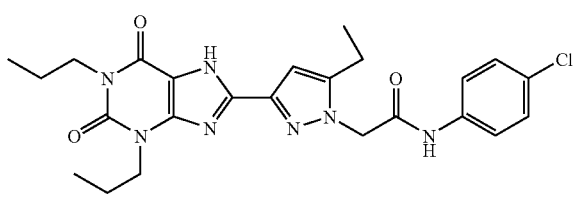

The title compound is prepared analogously to Example 1: m.p. 256-257° C.; $^1$H-NMR (DMSO-d$_6$) δ 0.88 (m, 6H), 1.25 (m, 3H), 1.55 (q, 2H), 1.70 (q, 2H), 2.66 (q, 2H), 3.84 (t, 2H), 3.99 (t, 2H), 5.08 (s, 2H), 6.77 (s, 1H), 7.40 (d, 2H J=7.6 Hz), 7.63 (d, 2H J=8.2 Hz), 10.56 (s, 1H), 13.67 (s, 1H).

EXAMPLE 10

2-[3-(2,6-Dioxo-1,3-dipropyl-2,3,6,7-tetrahydro-1H-purin-8-yl)-pyrazol-1-yl]-N-(4-chloro-phenyl)-acetamide

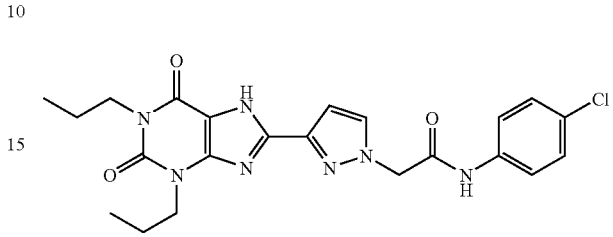

The title compound is prepared analogously to Example 1: m.p 283-285° C.; $^1$H-NMR (DMSO-d) δ 0.87 (m, 6H), 1.52 (q, 2H), 1.66 (q, 2H), 3.85 (t, 2H), 3.98 (t, 2H), 5.14 (s, 2H), 6.94 (d, 1H J=2.4 Hz), 7.37 (d, 2H J=8.8 Hz), 7.60 (d, 2H J=8.8 Hz), 7.89 (d, 1H J=2.6 Hz), 10.57 (s, 1H), 13.69 (s, 1H).

EXAMPLE 11

2-[3-(2,6-Dioxo-1,3-dipropyl-2,3,6,7-tetrahydro-1H-purin-8-yl)-5-methyl-pyrazol-1-yl]-N-(4-dimethylaminophenyl)-acetamide

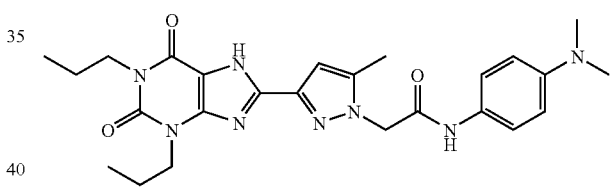

The title compound is prepared analogously to Example 1: m.p. >300° C.; $^1$H-NMR (DMSO-d$_6$) δ 0.88 (m, 6H), 1.56 (q, 2H), 1.70 (q, 2H), 2.31 (s, 3H), 2.84 (s, 6H), 3.85 (t, 2H), 3.94 (t, 2H), δ 5.01 (s, 2H), 6.67 (s, 1H), δ 6.72 (d, 2H J=9 Hz), 7.42 (d, 2H J=9 Hz), 10.11 (s, 1H), 13.70 (s, 1H).

EXAMPLE 12

2-[3-(2,6-Dioxo-1,3-dipropyl-2,3,6,7-tetrahydro-1H-purin-8-yl)-5-methyl-pyrazol-1-yl]-N-(4-sec-butylphenyl)-acetamide

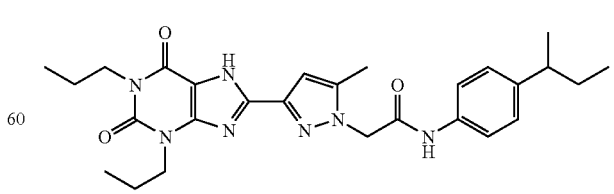

The title compound is prepared analogously to Example 1: m.p 268-271° C.; $^1$H-NMR DMSO-d$_6$ δ 0.74 (t, 3H); 0.88 (m, 6H); 1.15 (q, 3H); 1.48-1.55 (m, 7H); 2.31 (s, 3H); 3.85 (t, 2H); 3.97 (t, 2H); 5.06 (s, 2H); 6.74 (s, 1H); 7.14 (d, 2H); 7.49 (d, 2H); 10.33 (s, 1H); 13.75 (s, 1H).

EXAMPLE 13

2-[3-(2,6-Dioxo-1,3-dipropyl-2,3,6,7-tetrahydro-1H-purin-8-yl)-5-methyl-pyrazol-1-yl]-N-(naphthalen-1-yl)-acetamide

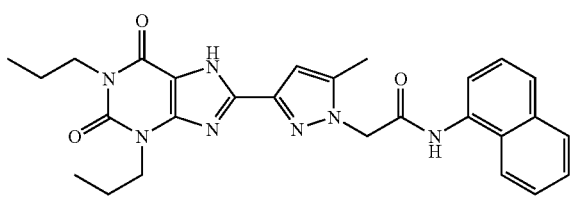

The title compound is prepared analogously to Example 1: m.p. >300° C.; $^1$H-NMR (DMSO-d$_6$) δ 0.89 (m, 6H), 1.59 (q, 2H), 1.72 (q, 2H), 2.36 (s, 3H), 3.85 (t, 2H), 3.97 (t, 2H), δ 30 (s, 2H), δ0.76 (s, 1H), 7.46-7.81 (m, 5H), 7.93-78.19 (m, 2H), 10.36 (s, 1H), 13.72 (s, 1H).

EXAMPLE 14

2-[3-(2,6-Dioxo-1,3-dipropyl-2,3,6,7-tetrahydro-1H-purin-8-yl)-5-methyl-pyrazol-1-yl]-N-(3-methoxy-lphenyl)-acetamide

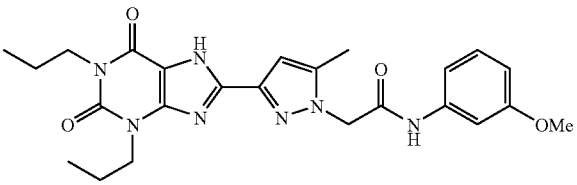

The title compound is prepared analogously to Example 1: m.p 274-277° C.; $^1$H-NMR (DMSO-d$_6$) δ 0.87 (m, 6H), 1.58 (q, 2H), 1.68 (q, 2H), 2.31 (s, 3H), 3.71 (s, 3H), 3.84 (t, 3H), 3.97 (t, 2H), δ0.06 (s, 2H), 6.63-6.68 (m, 1H), δ 72 (s, 1H), 7.08-7.31 (m, 3H), 10.48 (s, 1H), 13.80 (s, 1H).

EXAMPLE 15

2-[3-(2,6-Dioxo-1,3-dipropyl-2,3,6,7-tetrahydro-1H-purin-8-yl)-5-methyl-pyrazol-1-yl]-N-(3-chlorophenyl)-acetamide

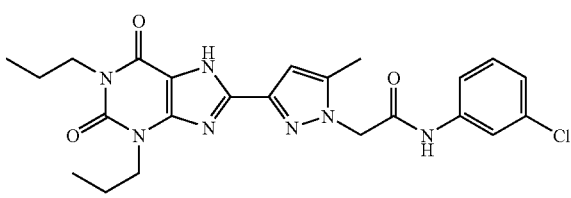

The title compound is prepared analogously to Example 1: m.p. 304-307° C.; $^1$H-NMR (DMSO-d$_6$) δ 0.87 (m, 6H), 1.56 (q, 2H), 1.70 (q, 2H), 2.31 (s, 3H), 3.84 (t, 2H), 3.95 (t, 2H), 5.09 (s, 2H), 6.73 (s, 1H), 7.15-7.80 (m, 4H), 10.48 (s, 1H), 13.80 (s, 1H).

EXAMPLE 16

2-[3-(2,6-Dioxo-1,3-dipropyl-2,3,6,7-tetrahydro-1H-purin-8-yl)-5-methyl-pyrazol-1-yl]-N-(3,4-dichlorophenyl)-acetamide

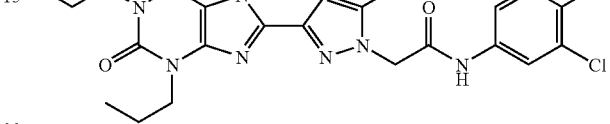

The title compound is prepared analogously to Example 1: m.p. 298° C.; $^1$H-NMR (DMSO-d$_6$) δ 0.87 (m, 6H), 1.57 (q, 2H), 1.73 (q, 2H), 2.31 (s, 3H), 3.86 (t, 2H), 3.95 (t, 2H), 5.01 (s, 2H), 6.75 (s, 1H), 7.47-7.59 (m, 2H), 7.97 (d, 1H), 10.73 (s, 1H), 13.75 (s, 1H).

EXAMPLE 17

2-[3-(2,6-Dioxo-1,3-dipropyl-2,3,6,7-tetrahydro-1H-purin-8-yl)-5-methyl-pyrazol-1-yl]-N-p-tolyl-acetamide

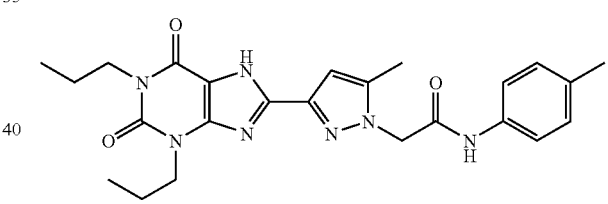

The title compound is prepared analogously to Example 1: m.p. >300° C.; $^1$H-NMR (DMSO-d$_6$) δ 0.88 (m, 6H), 1.57 (q, 2H), 1.72 (q, 2H), 2.25 (s, 3H), 2.31 (s, 3H), 3.84 (t, 2H), 3.99 (t, 2H), 5.05 (s, 2H), 6.73 (s, 1H), 7.20 (d, 2H J=8.8 Hz), 7.46 (d, 2H J=8.8 Hz), 10.32 (s, 1H), 13.85 (bs, 1H).

EXAMPLE 18

2-[4-Chloro-3-(2,6-dioxo-1,3-dipropyl-2,3,6,7-tetrahydro-1H-purin-8-yl)-5-methyl-pyrazol-1-yl]-N-(4-chlorophenyl)-acetamide

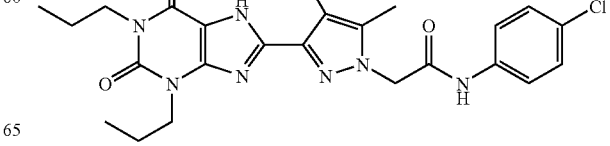

A. 4-Chloro-5-methyl-1H-pyrazole-3-carboxylic acid ethyl ester

To a magnetically stirred solution of ethyl 5-methyl-1H-pyrazole-3-carboxylate (3 mmol) in 10 mL of anhydrous DMF at 0° C. is added N-chlorosuccinimide (4 mmol). The solution is stirred at RT for 5 h. The solvent is concentrated to a half of the original volume, water is added and the reaction mixture is allowed to cool over ice. The solid that precipitates is collected by filtration and purified by crystallization to afford 4-chloro-5-methyl-1H-pyrazole-3-carboxylic acid ethyl ester as a white solid: m.p. 106-107° C.; $^1$H-NMR (DMSO-$d_6$) δ 1.25-1.32 (t, 3H J=7 Hz), 2.21 (s, 3H), 4.22-4.32 (q, 2H J=7.2), 13.59 (s, 1H).

B. 4-Chloro-1-[(4-chloro-phenylcarbamoyl)-methyl]-5-methyl-1H-pyrazole-3-carboxylic acid ethyl ester The title B compound is prepared as described for the title B compound of Example 1: m.p. 208-210° C.; $^1$H-NMR (DMSO-$d_8$) δ 1.26-1.29 (t, 3H J=72 Hz), 2.25 (s, 3H), 4.26-4.28 (q, 2H J=7.2 Hz), 5.14 (s, 2H), 7.39 (d, 2H J=8.8 Hz), 7.60 (d, 2H J=8.8 Hz), 10.60 (s, 1H).

C. 4-Chloro-1-[(4-chloro-phenylcarbamoyl)-methyl]-5-methyl-1H-pyrazole-3-carboxylic acid The title C compound is prepared as described for the title C compound of Example 1: m.p 244-245° C.; $^1$H-NMR (DMSO-$d_6$) δ 2.24 (s, 3H), 5.11 (s, 2H), 7.39 (d, 2H J=8.8 Hz), 7.60 (d, 2H J=8.8 Hz), 10.60 (s, 1H), 12.98 (s, 1H).

D. 2-[4-Chloro-3-(2,6-dioxo-1,3-dipropyl-2,3,6,7-tetrahydro-1H-purin-8-yl)-5-methyl-pyrazol-1-yl]-N-(4-chlorophenyl)-acetamide The title D compound is prepared as described for the title D compound of Example 1: m.p. 297-298° C.; $^1$H-NMR (DMSO-$d_6$) δ 0.88 (m, 6H), 1.62 (q, 2H), 1.70 (q, 2H), 2.31 (s, 3H), 3.85 (t, 2H), 4.00 (t, 2H), 5.15 (s, 2H), 7.39 (d, 2H J=9 Hz), 7.61 (d, 2H J=9 Hz), 10.59 (s, 1H), 13.89 (s, 1H).

EXAMPLE 19

2-[4-Bromo-3-(2,6-dioxo-1,3-dipropyl-2,3,6,7-tetrahydro-1H-purin-8-yl)-5-methyl-pyrazol-1-yl]-N-(4-chlorophenyl)-acetamide

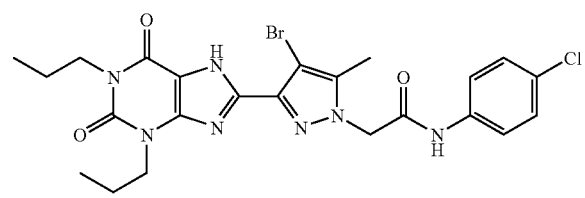

The title compound is prepared analogously to Example 18: m.p. 298-299° C.; $^1$H-NMR (DMSO-$d_6$) δ 0.88 (m, 6H), 1.57 (q, 2H), 1.72 (q, 2H), 2.321 (s, 3H), 3.91 (t, 2H), 4.02 (t, 2H), 5.19 (s, 2H), 7.39 (d, 2H J=9 Hz), 7.61 (d, 2H J=9 Hz), 10.68 (s, 1H), 13.79 (s, 1H).

EXAMPLE 20

2-[4-Iodo-3-(2,6-dioxo-1,3-dipropyl-2,3,6,7-tetrahydro-1H-purin-8-yl)-5-methyl-pyrazol-1-yl]-N-(4-chlorophenyl)-acetamide

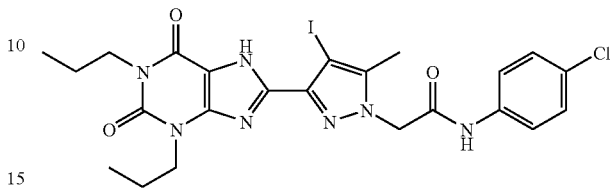

The title compound is prepared analogously to Example 18: m.p 296-297° C.; $^1$H-NMR (DMSO-$d_6$) δ 0.90 (m, 6H), 1.59 (q, 2H), 1.74 (q, 2H), 2.35 (s, 3H), 3.87 (t, 2H), 4.03 (t, 2H), 5.19 (s, 2H), 7.40 (d, 2H J=9 Hz), 7.59 (d, 2H J=9 Hz), 10.58 (s, 1H), 13.87 (s, 1H).

What is claimed is:

1. A compound of the formula

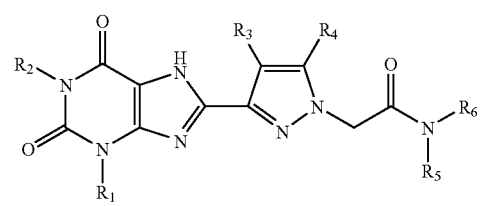

(I)

wherein
$R_1$ and $R_2$ are, independently from each other, $C_1$-$C_6$ alkyl optionally substituted by $C_1$-$C_4$ alkoxy, $C_3$-$C_6$ cycloalkyl, $C_2$-$C_4$ alkenyl, $C_2$-$C_4$ alkynyl or monocyclic aryl that may be optionally substituted by 1-3 substituents selected from the group consisting of $C_1$-$C_4$ alkyl, trifluoromethyl, halo, hydroxy, $C_1$-$C_4$ alkoxy, methylenedioxy, $C_1$-$C_4$ alkylthio, cyano, carboxy, $C_1$-$C_4$ alkoxycarbonyl, $C_1$-$C_4$ alkylthiono or $C_1$-$C_4$ alkylsulfonyl;
$R_3$ is hydrogen or halogen;
$R_4$ and $R_5$ are, independently from each other, hydrogen or $C_1$-$C_4$ alkyl;
$R_6$ is aryl or heteroaryl each of which may be optionally substituted by 1-3 substituents selected from the group consisting of $C_1$-$C_6$ alkyl, trifluoromethyl, $C_3$-$C_6$ cycloalkyl, halo, hydroxy, $C_1$-$C_6$ alkoxy, methylenedioxy, ethylenedioxy, $C_1$-$C_6$ alkanoyl, $C_1$-$C_6$ alkanoyloxy, $C_6$-$C_{10}$ aryloxy, amino, $C_1$-$C_6$ alkylamino, di($C_1$-$C_6$ alkyl)amino, $C_1$-$C_6$ alkylthio, $C_6$-$C_{10}$ arylthio, nitro, cyano, carboxy, $C_1$-$C_6$ alkoxycarbonyl, carbamoyl, $C_1$-$C_6$ alkylthiono, $C_1$-$C_6$ alkylsulfonyl or $C_6$-$C_{10}$ arylsulfonyl;
or a pharmaceutically acceptable salt thereof.

2. A compound according to claim 1, wherein
$R_3$ is hydrogen;
or a pharmaceutically acceptable salt thereof.

3. A compound according to claim 2, wherein
$R_5$ is hydrogen;
$R_6$ is monocyclic aryl which may be optionally substituted by 1-3 substituents selected from the group consisting of $C_1$-$C_6$ alkyl, trifluoromethyl, $C_3$-$C_6$ cycloalkyl, halo, hydroxy, $C_1$-$C_6$ alkoxy, methylenedioxy, ethylenedioxy, $C_1$-$C_6$ alkanoyl, $C_1$-$C_6$ alkanoyloxy, $C_6$-$C_{10}$ aryloxy, amino, $C_1$-$C_6$ alkylamino, di($C_1$-$C_6$ alkyl)amino, $C_1$-$C_6$ alkylthio, $C_6$-$C_{10}$ arylthio, nitro, cyano, carboxy, $C_1$-$C_6$ alkoxycarbonyl, carbamoyl, $C_1$-$C_6$ alkylthiono, $C_1$-$C_6$ alkylsulfonyl or $C_6$-$C_{10}$ arylsulfonyl;

or a pharmaceutically acceptable salt thereof.

4. A compound according to claim 3, wherein $R_1$ and $R_2$ are, independently from each other, $C_1$-$C_3$ alkyl optionally substituted by cyclopropyl, —CH=$CH_2$, —C≡CH or phenyl;

or a pharmaceutically acceptable salt thereof.

5. A compound according to claim 4, wherein $R_4$ is methyl;

or a pharmaceutically acceptable salt thereof.

6. A compound according to claim 1 selected from the group consisting of:

2-[3-(2,6-Dioxo-1,3-dipropyl-2,3,6,7-tetrahydro-1H-purin-8-yl)-5-methyl-pyrazol-1-yl]-N-phenyl-acetamide;

2-[3-(2,6-Dioxo-1,3-dipropyl-2,3,6,7-tetrahydro-1H-purin-8-yl)-5-methyl-pyrazol-1-yl]-N-(4-iodophenyl)-acetamide;

2-[3-(2,6-Dioxo-1,3-dipropyl-2,3,6,7-tetrahydro-1H-purin-8-yl)-5-methyl-pyrazol-1-yl]-N-(4-bromophenyl)acetamide;

2-[3-(2,6-Dioxo-1,3-dipropyl-2,3,6,7-tetrahydro-1H-purin-8-yl)-5-methyl-pyrazol-1-yl]-N-(4-chlorophenyl)-acetamide;

2-[3-(2,6-Dioxo-1,3-dipropyl-2,3,6,7-tetrahydro-1H-purin-8-yl)-5-methyl-pyrazol-1-yl]-N-(4-fluoro-phenyl)-acetamide;

2-[3-(2,6-Dioxo-1,3-dipropyl-2,3,6,7-tetrahydro-1H-purin-8-yl)-5-methyl-pyrazol-1-yl]-N-(4-methoxyphenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dimethylphenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dimethoxyphenyl)-acetamide;

2-[3-(2,6-Dioxo-1,3-dipropyl-2,3,6,7-tetrahydro-1H-purin-8-yl)-5-ethyl-pyrazol-1-yl]-N-(4-chlorophenyl)acetamide;

2-[3-(2,6-Dioxo-1,3-dipropyl-2,3,6,7-tetrahydro-1H-purin-8-yl)-pyrazol-1-yl]-N-(4-chloro-phenyl)-acetamide;

2-[3-(2,6-Dioxo-1,3-dipropyl-2,3,6,7-tetrahydro-1H-purin-8-yl)-5-methyl-pyrazol-1-yl]-N-(4-dimethylaminophenyl)-acetamide;

2-[3-(2,6-Dioxo-1,3-dipropyl-2,3,6,7-tetrahydro-1H-purin-8-yl)-5-methyl-pyrazol-1-yl]-N-(4-sec-butylphenyl)-acetamide;

2-[3-(2,6-Dioxo-1,3-dipropyl-2,3,6,7-tetrahydro-1H-purin-8-yl)-5-methyl-pyrazol-1-yl]-N-(naphthalen-1-yl)-acetamide;

2-[3-(2,6-Dioxo-1,3-dipropyl-2,3,6,7-tetrahydro-1H-purin-8-yl)-5-methyl-pyrazol-1-yl]-N-(3-methoxylphenyl)-acetamide;

2-[3-(2,6-Dioxo-1,3-dipropyl-2,3,6,7-tetrahydro-1H-purin-8-yl)-5-methyl-pyrazol-1-yl]-N-(3-chlorophenyl)-acetamide;

2-[3-(2,6-Dioxo-1,3-dipropyl-2,3,6,7-tetrahydro-1H-purin-8-yl)-5-methyl-pyrazol-1-yl]-N-(3,4-dichlorophenyl)-acetamide;

2-[3-(2,6-Dioxo-1,3-dipropyl-2,3,6,7-tetrahydro-1H-purin-8-yl)-5-methyl-pyrazol-1-yl]-N-p-tolyl-acetamide;

2-[4-Chloro-3-(2,6-dioxo-1,3-dipropyl-2,3,6,7-tetrahydro-1H-purin-8-yl)-5-methyl-pyrazol-1-yl]-N-(4-chlorophenyl)-acetamide;

2-[4-Bromo-3-(2,6-dioxo-1,3-dipropyl-2,3,6,7-tetrahydro-1H-purin-8-yl)-5-methyl-pyrazol-1-yl]-N-(4-chlorophenyl)-acetamide; and 2-[4-Iodo-3-(2,6-dioxo-1,3-dipropyl-2,3,6,7-tetrahydro-1H-purin-8-yl)-5-methyl-pyrazol-1-yl]-N-(4-chlorophenyl)-acetamide;

or a pharmaceutically acceptable salt thereof.

7. A pharmaceutical composition comprising a therapeutically effective amount of a compound of claim 1 in combination with one or more pharmaceutically acceptable carriers.

\* \* \* \* \*